United States Patent [19]

Hashizume et al.

[11] 4,175,859
[45] Nov. 27, 1979

[54] APPARATUS FOR AUTOMATED CLASSIFICATION OF WHITE BLOOD CELLS

[75] Inventors: Akihide Hashizume, Hachioji; Ryuichi Suzuki, Kokubunji; Hisatake Yokouchi, Hachioji; Hideyuki Horiuchi, Kokubunji; Shinji Yamamoto, Hachioji, all of Japan

[73] Assignee: Hitachi, Ltd., Japan

[21] Appl. No.: 815,824

[22] Filed: Jul. 14, 1977

[30] Foreign Application Priority Data

Jul. 23, 1976 [JP] Japan ................................. 51-87286

[51] Int. Cl.² ........................................... G01N 33/16
[52] U.S. Cl. ..................................... 356/39; 356/407; 364/416; 422/68
[58] Field of Search ............... 23/253 R; 356/39, 178, 356/179, 188, 407; 364/416, 526; 422/68

[56] References Cited

U.S. PATENT DOCUMENTS

| | | | |
|---|---|---|---|
| 3,315,229 | 4/1967 | Smithline | 356/39 X |
| 3,715,601 | 2/1973 | Tucker | 356/39 |
| 3,851,156 | 11/1974 | Green | 356/39 X |
| 3,919,530 | 11/1975 | Cheng | 364/526 X |
| 3,969,024 | 7/1976 | Hashizume et al. | 356/39 |
| 3,999,047 | 12/1976 | Green | 356/39 X |
| 4,000,417 | 12/1976 | Adkisson et al. | 356/39 X |
| 4,012,634 | 3/1977 | Bouton et al. | 356/39 X |

Primary Examiner—Michael S. Marcus
Attorney, Agent, or Firm—Craig and Antonelli

[57] ABSTRACT

An apparatus for automated classification of white blood cells comprising photo-electric converter means whereby the green and blue lights passing through the blood smear are converted into the respective electric signals, a first means for detecting the zone where the nucleus of white blood cell is present at a certain threshold level determined by the maximum and minimum values of the electric signal corresponding to green color, a second means for discriminating between the nucleus of white blood cell obtained from said first means and the granules and cytoplasm of white blood cell at a certain threshold level determined according to said electric signal corresponding to green color, a third means for discriminating between said cytoplasm and the back-ground at the threshold value determined on the basis of said electric signal corresponding to green color and obtained by adding a certain value to the average density on the back-ground, and a fourth means for discriminating between said nucleus and the red blood cells at a certain threshold level determined on the basis of said electric signal corresponding to blue color.

5 Claims, 12 Drawing Figures

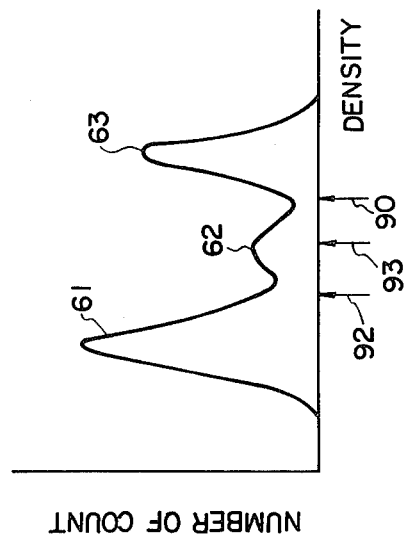
FIG. 6A
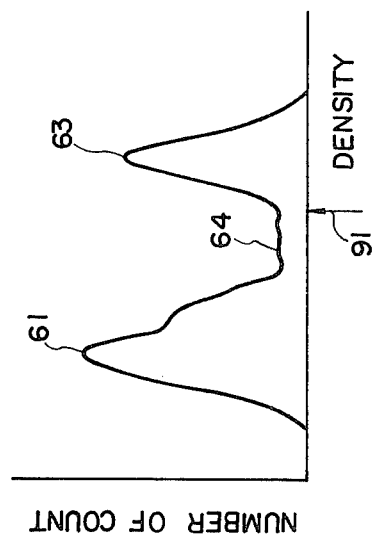
FIG. 6B
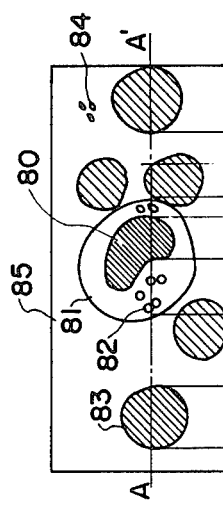
FIG. 2
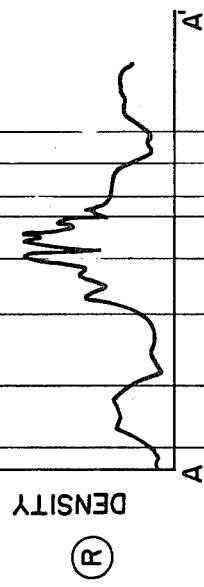
FIG. 3
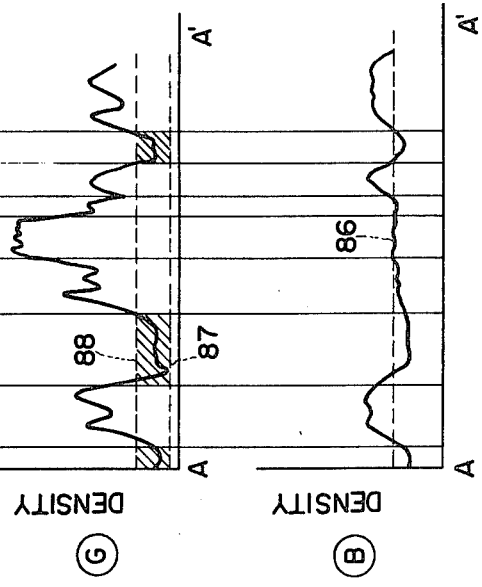
FIG. 4
FIG. 5

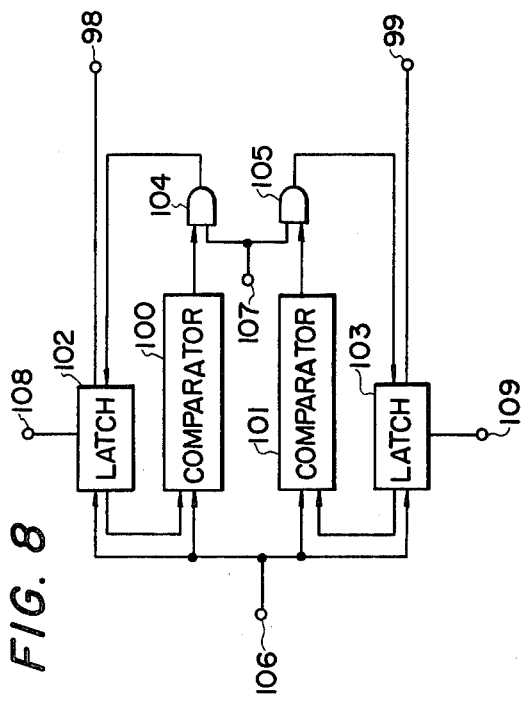
FIG. 8
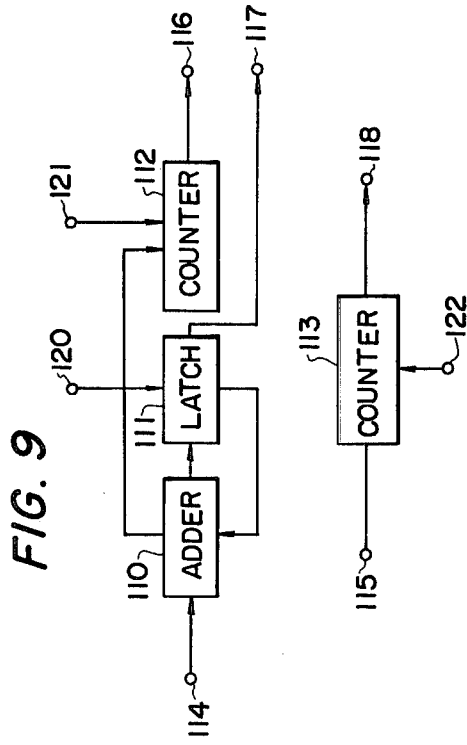
FIG. 9
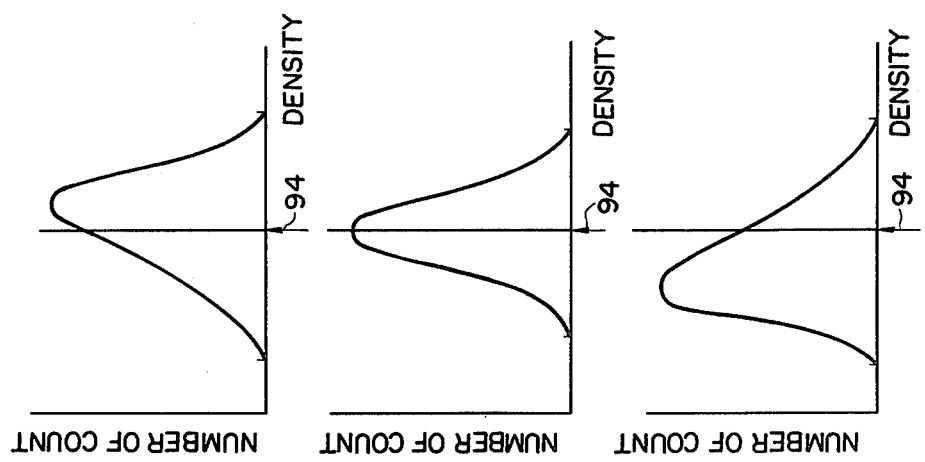
FIG. 7A
FIG. 7B
FIG. 7C

APPARATUS FOR AUTOMATED CLASSIFICATION OF WHITE BLOOD CELLS

BACKGROUND OF THE INVENTION

1. Field of the Invention

This invention relates to an automatic classifying apparatus for white blood cells, and more particularly to such apparatus which is capable of detecting the nucleus and cytoplasm of white blood cells by way of an electric signal corresponding to the light passing through the blood smear with a red, green or blue color filter being interposed therebetween.

2. Description of the Prior Art

Generally, the morphological, density and color informations of the nucleus and cytoplasm (including granules) of the white blood cell are the important factors in effecting classification of the white blood cells, and therefore it is essential to extract the nucleus and cytoplasm of the while blood cells in performing automatic classification of such blood cells. It is known, however, that in the case of a picture obtained by using white or single color light, the density level of the red blood cells or smudge existing in plurality around a white blood cell is very high and retards extraction of the nucleus and cytoplasm of the white blood cell. Therefore, in automatic classification of the white blood cells, it needs to eliminate the red blood cell and/or smudge image, which is a noise component, by using other means to allow stabilized extraction of the nucleus and cytoplasm image of the white blood cell. It is particularly noted that since said cytoplasm is not always high in density, discrimination thereof from the back-ground of the blood smear is very difficult. It is also necessary to extract and quantify the chromatin in the nucleus as density information.

SUMMARY OF THE INVENTION

The object of this invention is to provide an apparatus for detecting the nucleus and cytoplasm of white blood cell as well as the dense part of the nucleus accurately and quickly so as to detect the red blood cells and the back-ground with stability.

In order to accomplish such object, the present invention proposes the following novel techniques. First, the zone where the nucleus of white blood cell exists is detected from an electric signal corresponding to the light which has passed the blood smear through a green color filter (such electric signal being hereinafter referred to as G signal). Then, the nucleus in the thus detected zone is discriminated from the granules and cytoplasm of the white blood cell in said zone by using said G signal, and this is followed by further discrimination between the cytoplasm and the back-ground by dint of said G signal. After this, discrimination of said nucleus from the red blood cells is accomplished through an electric signal corresponding to the light which has passed the blood smear through a blue color filter (this signal being hereinafter referred to as B signal). Thereafter, the dense part of said nucleus is detected from an electric signal corresponding to the light which has passed the specimen through a red color filter (this signal being hereinafter referred to as R signal).

BRIEF DESCRIPTION OF THE DRAWINGS

FIG. 2 is a schematic illustration of a blood smear;

FIG. 3 is a graph showing the density change of the R signal obtained from the blood smear of FIG. 2;

FIG. 4 is a graph showing the density change of the G signal obtained from said blood smear;

FIG. 5 is a graph showing the density change of the B signal obtained from said blood smear;

FIG. 6A and FIG. 6B are density histograms of the G signal of the portion where the red blood cell image has been eliminated from the zone centered by the nucleus of a white blood cell;

FIG. 7A, FIG. 7B and FIG. 7C are diagrammatized nuclear density histograms of the R signal; and FIGS. 8 and 9 are diagrammatic drawings showing the principal parts of the embodiment shown in FIG. 1.

DESCRIPTION OF THE PREFERRED EMBODIMENT

Figure 1:
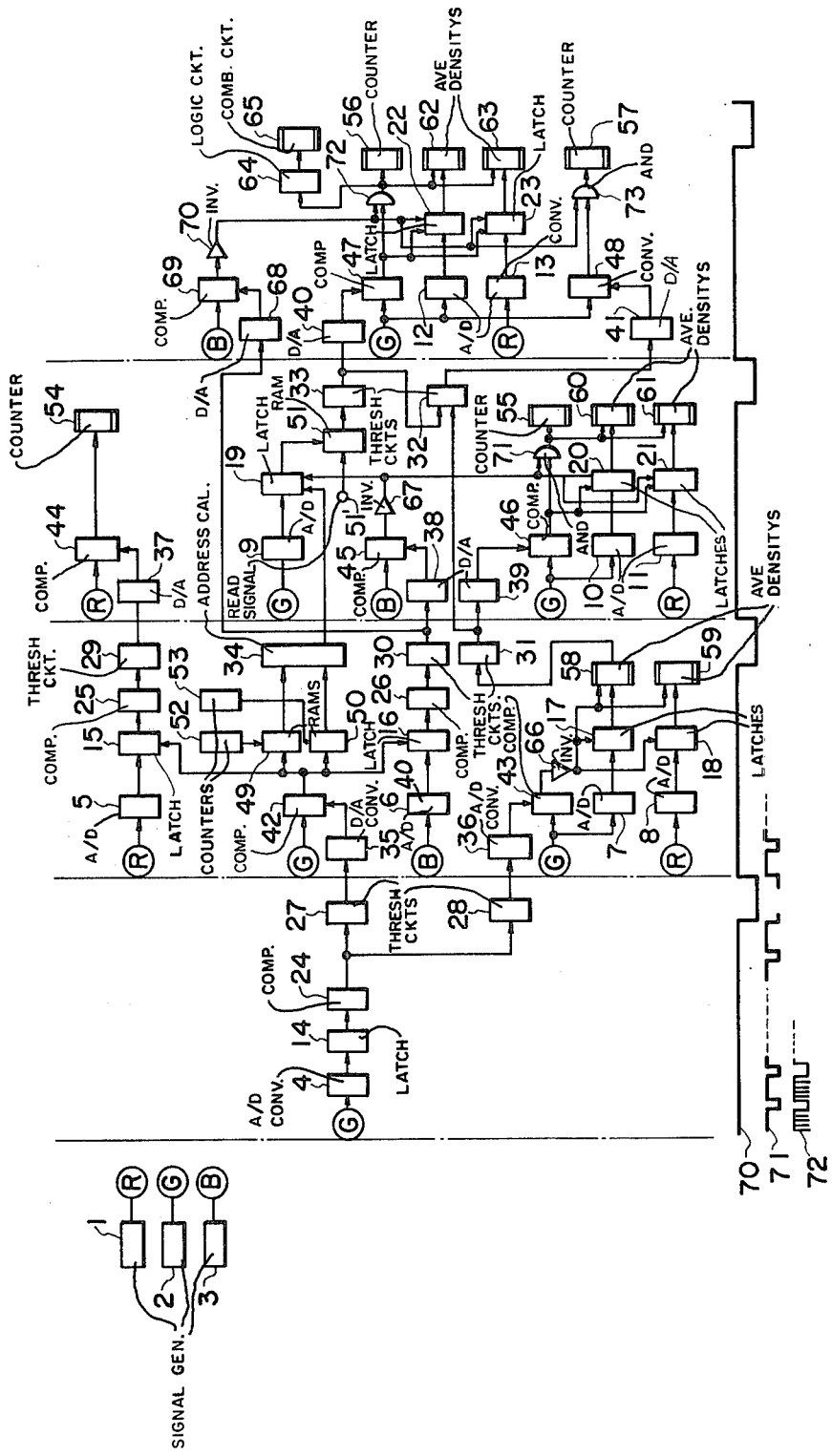
FIG. 1 is an arrangement plan showing an embodiment of this invention.

A schematic drawing of a blood smear subjected to an ordinary staining method (such as Wright staining, Giemsa staining, Wright-Giemsa staining, May-Giemsa staining, etc.) is shown in FIG. 2. In this drawing, there are schematically shown a nucleus 80 of a white blood cell, a cytoplasm 81 thereof, granules 82 thereof, red blood cells 83, platelets 84 and a back-ground 85. FIG. 3 shows R signal obtained through a red color filter (dominant wave length being approximately 680 nm), depicting the density variation on the line A—A' of FIG. 2, and FIG. 4 shows G signal obtained similarly through a green color filter (dominant wave length being approximately 550 nm), while FIG. 5 shows B signal also obtained in the similar way through a blue color filter (with dominant wave length of approximately 430 nm).

Above-said R, G and B signals are obtained by converting the lights which have passed the blood smear through a red color filter, a green color filter and a blue color filter, respectively, into the corresponding electric signals by means of a camera tube.

It is learned from FIGS. 3 to 5 that both nucleus and cytoplasm of the white blood cell can be extracted by making use of G signal which undergoes relatively small change of density corresponding to the chromatin.

As for the nucleus of the white blood cell, discrimination thereof from the granules and cytoplasm of the white blood cell as well as discrimination of said nucleus from the red blood cells existing in close proximity to said nucleus are required.

Therefore, in this invention, the zone where the nucleus of the white blood cell exists is first detected, and from this zone is determined the zone where the white blood cell is present. In this invention, G signal shown in FIG. 4 is used for the detection of such zone. That is, it is noted from the change of G signal that if 80% of the value of difference between the maximum and minimum values of G signal are given as threshold level and G signal with a value greater than such threshold level becomes the signal which indicates the nucleus portion. Thus, the zone where the white blood cell exists is determined from this signal. In order to accurately discriminate the nucleus portion from the granules and cytoplasm of the same white blood cell, there is employed a density histogram of the detected leukocyte-existing zone. FIG. 6A and FIG. 6B show such density histograms obtained from the variation of the G signal in the region where the red blood cells in said leucocyte-existing zone have been removed. Shown in FIG. 6A is the case where the granules are contained in the cytoplasm, and in this graph the peak 61 corresponds to the back-ground portion, the peak 62 corresponds to the cytoplasm and granule portion and the peak 63 corresponds to the nucleus portion. Therefore, it will be understood that, in the case of FIG. 6A, the value indicated by arrow 90, namely the minimum point appearing first on the maximum density side, becomes the threshold level. FIG. 6B shows the case where no granule is contained in the cytoplasm, and in this graph the spot indicated by 64 corresponds to the cytoplasm portion. Therefore, in the case of FIG. 6B, the value indicated by arrow 91, namely the flat point on the maximum density side, in other words, the point with small tilt (almost zero inclination) and small counted value, becomes the threshold level.

For removing the red blood cells, B signal shown in FIG. 5 is used. That is, it is known from the variation of B signal that when the maximum value (point indicated by 86) of the B signal in the said nucleus-existing zone is given as threshold level, the value greater than this threshold level represents the blood cell portion. And if this value is eliminated from the G signal of FIG. 4, the above-said histogram can be obtained from the G signal exclusive of the red blood cell zone.

As regards the cytoplasm of the white blood cell, the back-ground or the adjoining red blood cells are to be discriminated. In the case of the adjoining red blood cells, B signal may be used in the same way as elimination of the red blood cells at the time of nucleus detection. As the cytoplasm is not always high in density, its discrimination from the back-ground is fairly difficult. Also, it is susceptible to the influence of the signal variation. In order to solve this problem, first the minimum value (indicated by 87 in FIG. 4) of the G signal shown in FIG. 4 is determined and then a fixed value (indicated by 88 in FIG. 4) is added to this minimum value, and the area with the values smaller than the sum of said addition is regarded as the back-ground. The fixed value indicated by 88 shown in FIG. 4 is approximately 40 when 8-bit A/D conversion is made. Then the average density of this back-ground is obtained and $a_1$(20 to 25 when reduced by 8-bit A/D conversion) is added to the average density to determine the threshold level for discriminating the back-ground from the cytoplasm. The cytoplasm of the white blood cell can be extracted by these means.

When the threshold level for detecting the cytoplasm is obtained in FIG. 6A, as the peak 61 in the figure indicates the back-ground portion and the peak 62 indicates the portion where both cytoplasm and granules exist, the threshold level for detecting the cytoplasm to be discriminated from the back-ground takes the value indicated by arrow 92. Also in FIG. 6A, since the peak 62 shows the portion where both granules and cytoplasm exist and the arrow 90 shows the threshold level for discriminating the nucleus, the mean value (value of the point indicated by arrow 93) of the threshold levels indicated by arrows 92 and 90 become the threshold level for discriminating the granules from the cytoplasm.

It is also noted from FIG. 3 that the chromatin in the nucleus is emphasized by R signal. Therefore, the nuclear density histogram of such R signal may be represented as shown in FIG. 7A, FIG. 7B and FIG. 7C. FIG. 7A shows the density histogram of the nucleus with rough chromatin structure, FIG. 7B shows that of the nucleus with medium chromatin structure and FIG. 7C shows that of the nucleus with fine chromatin structure. Thus, if both maximum and minimum levels of R signal in the nucleus are obtained in these figures and their mean value is given as the threshold level (the value indicated by arrow 94 in the figures) to thereby define the dense part of the nucleus, it becomes possible to divide the nuclear chromatin into different structural groups.

According to the present invention, the above-described facts are advantageously incorporated to allow steady extraction of the nucleus and cytoplasm of the white blood cell as well as the dense part of the nucleus and then extraction of the red blood cells and back-ground.

Referring here to FIG. 1, there is shown a schematic arrangement plan of an embodiment of this invention utilizing the above-said R, G and B signals. In the figure, reference numerals 1, 2 and 3 designate the R signal, G signal and B signal generators, respectively, adapted for converting into the respective electric signals the lights which have passed the blood smear through the red, green and blue color filters, respectively. These signal generators 1-3 may be either photo-electric converters or the memory devices storing the signals converted by the photoelectric converter means, but here the photo-electric converters (camera tubes) are employed.

The G signal from the signal generator 2 is A/D converted by an A/D (analog to digital) converter 4 in pursuance to the clock signal, and the A/D conversion result is retained in a latch 14 to determine the maximum and minimum values by a digital comparator 24 designed to search the maximum and minimum values (shown in FIG. 8). These maximum and minimum values are used at two positions. During blanking of the vertical drive signal 70, first the threshold value (about 80% of the value of difference between the maximum and minimum values) for detecting the nucleus-existing zone is determined by a threshold calculation circuit 27 and this threshold value is D/A converted by a D/A converter 35 and given as reference voltage for the comparator 42. Then the threshold value for determining the average density of the back-ground is obtained from a threshold calculation circuit 28 and the obtained threshold value is D/A converted by a D/A converter 36 and given as reference voltage for the comparator 43. The foregoing is the first period processing of the vertical drive signal 70. The threshold calculation circuit 28 is composed of a minimum value detection circuit adapted for obtaining the minimum value of G signal and an adder adapted to add the output of said detection circuit and a signal (voltage) corresponding to a predetermined fixed value, and such threshold calculation circuit is of common knowledge for those skilled in the art. The output of said adder becomes the threshold level for determining the average density.

The threshold calculation circuit 27 is composed of a subtraction circuit adapted for determining the difference between the maximum and minimum values obtained from said digital comparator 24 and a comparator adapted to reduce the output of said subtraction circuit to the value of 80% thereof, and thus this calculation circuit is also of the type known in the art.

In the second period of the vertical drive signal 70, in order to determine the average density of the back-ground, G signal from the signal generator 2 is applied to the comparator 43 which has been given the output of the D/A converter 36 as reference voltage, and the output of said converter 43 is inverted by an inverter 66 so that the signal indicating "1" is produced for the back-ground and the signal "0" for the other parts. Also, G signal from the signal generator 2 and R signal from the signal generator 3 are A/D converted by A/D converters 7 and 8 and the conversion results are retained in the latches 17 and 18, respectively. The signal of said inverter 66 is used as the gate signal of said latches 17 and 18, and the average densities of the back-ground portions of both G and R signals are determined by the respective average density calculation circuits 58 and 59 (shown in FIG. 9). The output of said average density calculation circuit 58 is led into a threshold calculation circuit 31 to determine the threshold value for discriminating between the back-ground and the cytoplasm, and this threshold value is D/A converted by a D/A converter 39 and provided as reference voltage for the comparator 46. The output of the signal generator 2 is applied as another input to the comparator 46 to produce the signal "1" for the cytoplasm (including nucleus, granules and a part of red blood cells) and the signal "0" for the other parts.

The threshold calculation circuit 31 comprises an adder for adding a predetermined value $\alpha_1$ to the output of the average density calculation means 58, and the mechanism of such circuit is known in the art.

As means for setting the zone where the white blood cells exist, G signal from the signal generator 2 is applied to the comparator 42 provided with the output of the D/A converter 35 as reference voltage, so as to produce the nucleus-existence indicating signal "1" for the nucleus of white blood cell and "0" for the other parts. A projected histogram for both horizontal and vertical directions of the signal indicating existence of the nucleus of white blood cell is made by using the output signal of said comparator 42 as the addition signal of RAM 49 and 50 adapted for addressing the output of a counter 52 which counts up the signal according to the horizontal drive signal and the output of a counter 53 which counts up according to the clock signal. The contents of RAM 49 indicate, by a binary value, the length on the sampling line in the horizontal direction of the leukocyte nucleus-existing portion and the contents of RAM 50 indicate the length on the sampling line in the vertical direction of said portion. Therefore, the position of white blood cell in the vertical direction in the picture is determined from the contents of RAM 49 and the position of white blood cell in the horizontal direction is determined from the contents of RAM 50.

The outputs of said RAM 49 and 50 are fed into an address calculation means 34 to thereby determine the leukocyte-existing zone.

The following operation is performed in said address calculating means 34.

In order to eliminate noise, a frequency greater than a certain given value, that is, a position greater than a certain given length is determined. In this case, the upper and lower limits of the position of the white blood cells is determined from the contents of RAM 49, while the right and left limits of said position are determined from the contents of RAM 50. The leukocyte-existing position is plotted by means of coordinates, with the middle point between said upper and lower limits as ordinate and with the middle point between said right and left limits as abscissa, and in these coordinates, the area provided by expanding vertically by an amount given by adding a fixed value (in this case 15 as sampled at 0.3 $\mu$pits) to the half of the difference between the upper and lower limits and horizontally by an amount given by adding said fixed value to the half of the difference between the right and left limits is determined as the zone where the white blood cells exist. Such operational processing is performed through a predetermined processing operation by a computer used as the address calculation circuit 34.

For obtaining the maximum and minimum values in the nucleus of white blood cell, R and B signals from the signal generators 1 and 3 are A/D converted by the respective A/D converters 5 and 6 and the results are retained in the latches 15 and 16. By using the nucleus existence indicating signal from said comparator 42 as the gate signal of said latches 15 and 16, the maximum and minimum value of both R and B signals in the nucleus are obtained from the respective digital comparators 25 and 26. The threshold value (middle value between the maximum and minimum values) for extracting the dense part of nucleus is determined from the output of said digital comparator 25 by the threshold calculation means 29, and the determined threshold value is D/A converted by a D/A converter 37 to provide it as reference voltage for the comparator 44. On the other hand, the threshold value (maximum value of B signal) for extracting the red blood cells is determined from the output of said digital comparator 26 by the threshold calculation means 30 and such threshold value is D/A converted by the D/A converters 38, 68 to provide reference voltage for the comparators 45, 69.

The threshold calculation means 29 consists of an adder adapted to add the maximum and minimum values obtained from the digital comparator 25 and a divider adapted to halve the output of said adder, and hence such means is well known in the art. The threshold calculation means 30 comprises a maximum value detection circuit adapted to detect the maximum value from the output of the digital comparator 26, and such means is also obvious to those skilled in the art.

In the third period in which the dense part of nucleus is to be extracted, R signal from the signal generator 1 is applied to the comparator 44 which was given the output of the D/A converter 37 as reference voltage, and the output of said comparator 44 is counted by a counter 54 to determine the size of the dense part of nucleus. Then G signal from the signal generator 2 is A/D converted by the A/D converter 9 and retained in the latch 19. On the other hand, B signal from the signal generator 3 is fed to the comparator 45 having the output of the D/A converter 38 as reference voltage and the output of said comparator 45 is inverted by an inverter 67 so as to produce the signal "1" for the red blood cells and "0" for the other parts. The outputs of said inverter 67 and address calculation means 34 are used as gate signal of the latch 19. As the G signal which has been A/D converted by the A/D converter 9 is applied to the latch 19 as the contents of said latch 19, the leukocyte-existing zone is determined by the gate signal from the address calculation means 34, and if any red blood cell exists in this zone, the output "1" of the inverter 67 becomes the gate signal of the latch 19 and the contents of said latch 19 won't be sent to RAM 51. However, if no red blood cell is present in said zone, the contents of the latch 19 are supplied to RAM 51. Thus, the output of the latch 19 is used as address signal of RAM 51. From this processing, there can be obtained a density histogram of the leukocyte-existing zone free of the red blood cells. The threshold level for discriminating the nucleus from the granules and cytoplasm is determined by the threshold calculation means 33 from the output of said RAM 51 (such output being given by read signal applied from the terminal 51'), and this threshold value is D/A converted by the D/A converter 40 and given as reference voltage for the comparator 47.

In the threshold detection circuit 33, processing is started from the maximum density side and ended upon finding the first minimum point or flat point. In the case of FIG. 6A, the point at which the inclination changes from positive to negative is the optimum threshold value for detecting the nucleus, and in the case of FIG. 6B, the point at which both inclination and counted value are small is the optimum threshold value.

Such detection of the threshold value is accomplished through a predetermined processing operation by a computer used as the threshold detection means 33.

Also, the outputs of the threshold calculation means 33 and 31 (threshold value for detecting the nucleus and threshold value for detecting the cytoplasm) are supplied to the threshold calculation circuit 32 and the mean of both threshold values is obtained. That is, the output of the calculation circuit 32 is provided as the threshold level for discriminating the granules from the cytoplasm. The threshold calculation means 32 is composed of an adder which receives the outputs of the threshold calculation means 33 and 31 and a divider which halves the output of said adder, and such calculation means is of the type generally known in the art.

The above-described means and processing according to this invention make it possible to detect the white blood cell with its nucleus, cytoplasm and granules being discriminated from the red blood cells and background. After the foregoing process, it is required to further determine the average density and size of each detected part as well as the nuclear perimeter length and the number of nuclear segments, but as means for determining these matters are not directly related to the cause of this invention, they are only roughly explained below.

First, as a part of the processing operation in the third period of the vertical drive signal 70, the outputs of the signal generators 2 and 3 are A/D converted by the respective A/D converters 10 and 11, and their results are retained in the latches 20 and 21. Then, by using the outputs of the inverter 67 and comparator 46 as gate signal of said latches 20, 21, the average density of the cytoplasm portion (including nucleus and granules) of the green and red signals are determined by the average density calculation means 60, 61. The cytoplasm size is also determined by counting the outputs of said inverter 67 and comparator 46 by the counter 55 through an AND circuit 71.

In the fourth period, as the processing operation for determining the average density and size of the nucleus, the output of the signal generator 2 is fed into the comparator 47 provided with the output of the D/A converter 40 as reference voltage, so as to produce the signal of "1" for the nucleus (including part of red blood cells) and "0" for the other parts. Also, the output of the signal generator 3 is input to the comparator 69 given the output of the D/A converter 68 as reference voltage so as to produce the signal "1" for the red blood cells and "0" for the other parts. On the other hand, the output of the signal generator 2 is A/D converted by the A/D converters 12 and 13 and the results of A/D conversion are retained in the respective latches 22 and 23. Then the average densities of the nucleus portions of both G and R signals are determined by the respective average density calculation means 62 and 63 by using the outputs of the inverter 70 and comparator 47 as gate signal of said latches 22 and 23. Further, the nuclear size can be determined by counting the outputs of said inverter 70 and comparator 47 by the counter 56 through an AND circuit 72.

For determining the size of the granule (including nucleus), the output of the signal generator 2 is fed into the comparator 48 supplied with the output of the D/A converter 41 as reference voltage, and the signal "1" is produced for the granules (including nucleus and a part of red blood cells) and "0" signal for the other parts. Also, the size of the granule portion (including nucleus) is determined by counting the outputs of said comparator 48 and inverter 70 by the counter 57 through an AND circuit 73. Further, the nuclear perimeter length and the number of nuclear segments can be determined by applying the output of the AND circuit 72 to a 2×2 logic circuit 64 and counting the result thereof by a combinatorial circuit 65.

Now, the structural arrangements of the digital circuits for searching the maximum and minimum values and the average density calculation circuits used in the embodiment shown in FIG. 1 are described.

Referring to FIG. 8, there is shown a schematic drawing illustrating the structural arrangement of the digital comparators 24, 25 and 26. In the shown circuit arrangement, the contents of the latches 102, 103 are read to the respective output terminals 98, 99 at the front edge of the vertical drive signal 70 (applied to the latches 102, 103 via the input terminals 108, 109), and at the rear edge of said vertical drive signal 70 the latch 102 is set to "0" and the latch 103 is set to the source voltage (maximum value). The input from the input terminal 106 (which is given the output from for example the latch 14) is led to the comparators 100, 101, while the contents of the latches 102, 103 are also given to the respective comparators 100, 101. When the imput from the input terminal 106 is greater than the contents of the latch 102, the comparator 100 outputs "1" to render the gate 104 into the "on" state. In this situation, clock 72 passes the gate 104 via the input terminal 107 to set the input from the input terminal 106 to the latch 102. When the input from the input terminal 106 is smaller than the contents of the latch 103, the comparator 101 outputs "1" to turn the gate 105 into the "on" state. As this stage is reached, clock 72 passes the gate 105 via the input terminal 107 to set the input from the input terminal 106 to the latch 103. Thus, the input given through the input terminal 106 is set to the respective latches 102 and 103 by the outputs from the gate circuits 104 and 105, and consequently the comparison between the contents of the latches 102, 103 and the input applied through said input terminal 106 is performed in the comparators 100 and 101.

FIG. 9 shows the structural arrangement of the average density calculation means 58, 59, 60, 61, 62 and 63 shown in FIG. 1. The contents of the latch 111 and counters 112, 113 are read to the respective output terminals 117, 116, 118 at the front edge of the vertical drive signal 70 (applied via the input terminals 120, 121 and 122), and the latch 111 and counters 112, 113 are set to "0" at the rear edge of the vertical drive signal 70.

The signal from the input terminal 114 (for example the output signal from the latch 17) and the contents of the latch 111 are applied to an adder 110 and added thereby, and if there is any overflow, it is counted in the counter 112 and the contents of the adder 110 are retained in the latch 111. On the other hand, the signal from the input terminal 115 (for example, the output signal from the inverter 66) is counted by the counter 113.

The contents of the output terminal 118 indicate the size (for example the size of the dense part detected as the back-ground), and when 8-bit A/D conversion is made, the output terminal 116 expresses the value of the upper 8 bits while the output terminal 117 expresses the value of the lower 8 bits, so that if the outputs of the output terminals 116, 117 are supposed to be a 16-bit figure and this is divided by the contents of the output terminal 118 (the divider therefor being not shown), the average density is given.

What is claimed is:

1. An apparatus for automated classification of white blood cells, comprising:

means for generating light having components of at least one of green light, blue light and red light and for passing the light through a blood specimen;

green light converting means for converting the green light passing the blood specimen into an electric output signal;

first detecting means for detecting the maximum and minimum values of the output signal produced from said green light converting means and providing maximum and minimum value output signals;

difference means for detecting the difference between the maximum and minimum value output signals provided from said first detecting means and producing an output signal which is a predetermined percentage of said detected difference;

second detecting means for detecting the output signal of said green light converting means greater than the output signal of said difference means and providing an output signal for indicating the zone where the nucleus of white blood cells exists;

blue light converting means for converting the blue light passing the blood specimen into an electric output signal;

maximum value means for detecting the maximum value from the output signal produced from said blue light converting means and providing a maximum value output signal;

third detecting means for detecting, from the output signal produced from said blue light converting means, the values greater than the output signal from said maximum value means;

position means by which the positions in both horizontal and vertical directions of the white blood cells in the blood specimen are detected from the output signal produced from said second detecting means and providing the output signal indicative thereof;

address calculation means controlled by the output signal from said position means and storing the output signal from said green light converting means when there exists no output signal from said third detecting means and providing an output signal; and minimum value means for detecting the minimum value which is produced at the termination of variation of the output signal from said address calculation means and providing a minimum value signal for indicating the nucleus of the white blood cell.

2. An apparatus for automated classification of white blood cells as set forth in claim 1, further comprising:

additional minimum value means for detecting the minimum value signal produced from said first detecting means and for producing an output signal;

fourth detecting means for detecting, from the output signal produced from said green light converting means, the values smaller than the value formed by a fixed value added to the output signal produced from said additional minimum value means and for producing an output signal;

average value means for determining the averge value of the output signal produced from said smaller value means and for producing an output signal;

adder means for adding a predetermined value to the output signal from said average value means and for producing an output signal; and another average value means for determining the average value of the output signal from said minimum value means and the output signal from said adder means, wherein the average value of the average value means is utilized as a signal for indicating the cytoplasm and granule of the white blood cell.

3. The apparatus for automated classification of white blood cells as set forth in claim 1, wherein said minimum value means serves for detecting, from the output signal of said address calculation means, those values of the output signal which make the inclination substantially zero.

4. An apparatus for automated classification of white blood cells, comprising:

means for generating light having components of at least one of green light, blue light and red light and passing the light through a blood specimen;

green light converting means for converting the green light passing the blood specimen into an electric output signal;

first detecting means for detecting the maximum and minimum values of the output signal produced from said green light converting means and providing maximum and minimum output signal;

difference means for detecting the difference between the maximum and minimum value output signals provided from said first detecting means and producing an output signal which is a predetermined percentage of said detected difference;

second detecting means for detecting the output signal of said green light converting means greater than the output signal of said difference means and providing an output signal utilized as a signal for indicating the zone where the nucleus of white blood cells exists;

minimum value means for detecting the minimum value produced from said first detecting means and for producng an output signal;

third detecting means for detecting, from the output signal produced from said green light converting means, the values smaller than the value formed by a fixed value added to the output signal produced from said minimum value means and for producing an output signal;

average value means for detecting the average value of the output signal produced from said third detecting means and for producing an output signal;

adder means for adding a predetermined value of the output signal from said average value means and for producing an output signal; and fourth detecting means for detecting the output signal of said green light converting means greater than the output signal of said adder means, wherein the output signal of said fourth detecting means is used as a signal for indicating the cytoplasm of the white blood cell.

5. An apparatus for automated classification of white blood cells, comprising:

means for generating light having components of at least one of green light, blue light and red light and for passing the light through a blood specimen;

green light converting means for converting the green light passing the blood specimen into an electric output signal;

first detecting means for detecting the maximum and minimum values of the output signal produced from said green light converting means and providing maximum and minimum value output signals;

difference means for detecting the difference between the maximum and minimum value output signals provided from said first detecting means and producing an output signal which is a predetermined percentage of said detected difference and providing an output signal;

second detecting means for detecting the output signal of said green light converting means greater than the output signal of said difference means and providing an output signal for indicating the zone where the nucleus of white blood cells exists;

red light converting means for converting the red light passing the blood specimen into an electric output signal;

retaining means controlled by the output of said second detecting means and retaining the output signal from said red light converting means and providing an output signal;

maximum-minimum value means for detecting the maximum and minimum values from the output signal of said retaining means and providing maximum and minimum value output signals;

averaging means for determining the average of the maximum and minimum value output signals obtained from said maximum-minimum value means and providing an output signal;

third detecting means for detecting the output signal of said red light converting means larger than the output signal from said averaging means; and counting means for counting the output of said third detecting means and providing an output utilized as a signal for indicating the dense part of the nucleus of white blood cell.

* * * * *